United States Patent
Brooks et al.

(10) Patent No.: US 10,085,838 B2
(45) Date of Patent: Oct. 2, 2018

(54) ASSEMBLY TOOL

(71) Applicant: DEPUY (IRELAND), County Cork (IE)

(72) Inventors: James Brooks, Leeds (GB); Jonathan Thompson, Leeds (GB)

(73) Assignee: DEPUY IRELAND UNLIMITED COMPANY (IE)

(*) Notice: Subject to any disclaimer, the term of this patent is extended or adjusted under 35 U.S.C. 154(b) by 150 days.

(21) Appl. No.: 14/995,617

(22) Filed: Jan. 14, 2016

(65) Prior Publication Data

US 2016/0206443 A1 Jul. 21, 2016

Related U.S. Application Data

(60) Provisional application No. 62/103,611, filed on Jan. 15, 2015.

(51) Int. Cl.
*A61F 2/30* (2006.01)
*A61F 2/36* (2006.01)
*A61F 2/46* (2006.01)
*B23P 19/02* (2006.01)

(52) U.S. Cl.
CPC .............. *A61F 2/3094* (2013.01); *A61F 2/36* (2013.01); *A61F 2/3609* (2013.01); *A61F 2/3662* (2013.01); *A61F 2/4637* (2013.01); *B23P 19/02* (2013.01); *A61F 2002/30332* (2013.01); *A61F 2002/30471* (2013.01); *A61F 2002/30553* (2013.01); *A61F 2002/365* (2013.01); *A61F 2002/3625* (2013.01); *A61F 2002/3627* (2013.01); *A61F 2002/3652* (2013.01); *A61F 2002/4627* (2013.01); *A61F 2002/4629* (2013.01); *A61F 2002/4638* (2013.01); *A61F 2002/4687* (2013.01); *A61F 2240/001* (2013.01)

(58) Field of Classification Search
CPC ........ A61F 2/36; A61F 2/3609; A61F 2/3804; A61F 2002/3809; A61F 2002/3822; A61F 2/3094
See application file for complete search history.

(56) References Cited

U.S. PATENT DOCUMENTS

| 1,435,278 A | 11/1922 | Campbell |
| 1,595,658 A | 8/1926 | Heinrich |
| 1,794,494 A | 3/1931 | Noble |
| 2,190,585 A | 2/1940 | Rhinevault |
| 2,408,801 A | 10/1946 | Miller |

(Continued)

FOREIGN PATENT DOCUMENTS

| DE | 29824993 U1 | 1/2004 |
| DE | 202012102017 U1 | 10/2013 |

(Continued)

*Primary Examiner* — Jason-Dennis Stewart (57) ABSTRACT

An instrument for assembling an implant on a neck. The implant and neck being coupled via a taper having a taper axis. The instrument includes a frame having a distal portion and a proximal portion, the distal portion of the frame including a retaining member adapted to engage a portion of the neck. The instrument also includes a force applier retained in the proximal portion of the frame. The force applier includes a screw having a screw axis that is coaxial with the taper axis, wherein the screw is adapted to engage the implant. As the screw is turned, the force applier applies a force on the implant while the neck is held in place by the frame, thereby causing the tapers of the implant and neck to engage.

12 Claims, 9 Drawing Sheets

(56) References Cited

U.S. PATENT DOCUMENTS

| | | |
|---|---|---|
| 2,863,477 A | 12/1958 | Sagerty |
| 3,102,536 A | 9/1963 | Rose |
| 3,801,989 A | 4/1974 | McKee |
| 4,705,520 A | 11/1987 | Ahrens |
| 4,795,472 A | 1/1989 | Crowninshield |
| 4,865,609 A | 9/1989 | Roche |
| 5,133,765 A | 7/1992 | Cuilleron |
| 5,171,324 A | 12/1992 | Campana |
| 5,849,015 A | 12/1998 | Haywood |
| 5,966,792 A | 10/1999 | James |
| 6,113,605 A | 9/2000 | Storer |
| 6,629,982 B2 | 10/2003 | Day |
| 7,497,875 B1 | 3/2009 | Zweymuller |
| 7,661,162 B2 | 2/2010 | Soerensen |
| 7,699,847 B2 | 4/2010 | Sheldon |
| 8,152,855 B2 | 4/2012 | Tulkis |
| 8,518,050 B2 | 8/2013 | McCleary |
| 8,533,921 B2 | 9/2013 | Leisinger |
| 2004/0267373 A1 | 12/2004 | Dwyer |
| 2007/0162038 A1 | 7/2007 | Tuke |
| 2009/0281632 A1 | 11/2009 | Naidu |
| 2011/0009976 A1 | 1/2011 | Cruchet |
| 2012/0253469 A1 | 10/2012 | Collins |
| 2012/0259338 A1 | 10/2012 | Carr |
| 2016/0206430 A1 | 7/2016 | Grostefon |
| 2016/0206443 A1 | 7/2016 | Brooks |
| 2016/0206444 A1 | 7/2016 | Schmalzried |
| 2016/0206445 A1 | 7/2016 | Gheevarughese |

FOREIGN PATENT DOCUMENTS

| | | |
|---|---|---|
| EP | 200672 A1 | 11/1986 |
| EP | 1080701 A2 | 3/2001 |
| EP | 1437107 A1 | 7/2004 |
| EP | 1776937 A1 | 4/2007 |
| WO | WO 2000059410 A2 | 10/2000 |
| WO | WO 2016115359 A1 | 7/2016 |
| WO | WO 2016115364 A1 | 7/2016 |
| WO | WO 2016115365 A1 | 7/2016 |

Fig. 11

ASSEMBLY TOOL

CROSS REFERENCE TO RELATED APPLICATION

This application claims priority under 35 U.S.C. § 119 to U.S. Patent App. Ser. No. 62/103,611 entitled "ASSEMBLY TOOL," which was filed Jan. 15, 2015 and is expressly incorporated herein by reference.

Cross-reference is made to U.S. Patent App. Ser. No. 62/103,826 entitled "FEMORAL STEM INCLUDING AN ANCHOR TO FACILITATE ASSEMBLY AND IMPLANTATION," which was filed Jan. 15, 2015 and is expressly incorporated herein by reference.

TECHNICAL FIELD OF THE INVENTION

The present invention relates generally to the field of orthopedics, and, more particularly, to an instrument for assembling a head to a stem.

BACKGROUND

A joint within the human body forms a juncture between two or more bones or other skeletal parts. The ankle, hip, knee, shoulder, elbow and wrist are just a few examples of the multitude of joints found within the body. As should be apparent from the above list of examples of joints, many of the joints permit relative motion between the bones. For example, the ankle permits a hinge movement, the knee allows for a combination of gliding and hinge movements and the shoulder and hip permit movement through a ball and socket arrangement.

The joints in the body are stressed or can be damaged in a variety of ways. Gradual wear and tear is imposed on the joints through the continuous use of a joint over the years. The joints that permit motion have cartilage positioned between the bones providing lubrication to the motion and also absorbing some of the forces direct for the joint. Over time, the normal use of a joint may wear down the cartilage and bring the moving bones in a direct contact with each other. In contrast, in normal use, a trauma to a joint, such as the delivery of a large force from an automobile accident for example, may cause considerable damage to the bones, the cartilage or to other connective tissue such as tendons or ligaments.

Arthropathy, a term referring to a disease of the joint, is another way in which a joint may become damaged. One form of joint disease is arthritis, which is generally referred to a disease or inflammation of a joint that results in pain, swelling, stiffness, instability, and often deformity.

There are many different forms of arthritis, with osteoarthritis being the most common and resulting from the wear and tear of a cartilage within a joint. Another type of arthropathy is osteonecrosis, which is caused by the death of a part of the bone due to loss of blood supply and subsequent degeneration of the cartilage. Other types of arthritis are caused by trauma to the joint while others, such as rheumatoid arthritis, Lupus, and psoriatic arthritis destroy cartilage and are associated with the inflammation of the joint lining.

The hip joint is one of the joints that is commonly afflicted. The hip joint is a ball and socket joint that joins the femur or thighbone with the pelvis. The pelvis has a hemispherical socket called the acetabulum for receiving the head of the femur. Both the head of the femur and the acetabulum are coated with cartilage for allowing the femur to articulate within the pelvis. Other joints commonly afflicted include those of the spine, knee, shoulder, elbow, carpals, metacarpals, and phalanges of the hand. One means to address this affliction is arthroplasty which commonly refers to the making of an artificial joint. In severe cases of arthritis or other forms of arthropathy, such as when pain is overwhelming or when a joint has a limited range of mobility, a partial or total replacement of the joint may be justified. The procedure for replacing the joint varies, of course, with the particular joint in question, but in general involves replacing a terminal portion of an afflicted bone with a prosthetic implant and inserting a member with structural support to serve as a substitute for the cartilage.

The prosthetic implant is formed of a rigid material that becomes bonded with the bone and provides strength and rigidity to the joint and a bearing member chosen to allow for lubrication to the joint. Suitable materials for the implant include metals and composite materials such as titanium, cobalt chromium, stainless steel, ceramic and suitable materials for the bearing include polyethylene, metal and ceramics. A cement may also be used to secure the prosthetic implant to the host bone.

Total hip replacement, for example, involves removing the ball shaped head of the femur and inserting a stemmed implant into the center of the bone, which is referred to as the medullary canal of the bone. The stem implant may be cemented into the medullary canal or may have a porous coated surface for allowing the bone to heal directly to the implant. The stemmed implant has a neck and a ball shaped head, which are intended to perform the same functions as the neck and head of a healthy femur. In some implants, the head is attached to the neck via a taper connection. It is important to assemble the head to the neck with enough force so as to limit micromotion between the head and neck. The acetabulum of the patient is reamed to receive a shell and liner. A polyethylene, metal or ceramic liner with a metal shell is inserted into the acetabulum and acts as socket for receiving the head on the stemmed implant.

While performing the surgery, it would be beneficial to have an instrument that can easily and with certainty assemble the head to the neck.

SUMMARY OF THE INVENTION

According to one embodiment of the present invention, an instrument for assembling an implant on a neck is provided. The implant and neck being coupled via a taper having a taper axis. The instrument includes a frame having a distal portion and a proximal portion, the distal portion of the frame including a retaining member adapted to engage a portion of the neck. The instrument also includes a force applier retained in the proximal portion of the frame. The force applier includes a screw having a screw axis that is coaxial with the taper axis, wherein the screw is adapted to engage the implant. As the screw is turned, the force applier applies a force on the implant while the neck is held in place by the frame, thereby causing the tapers of the implant and neck to engage.

According to another embodiment of the present invention, a system for hip orthopaedic surgery is provided. The system includes a neck, an implant, and an instrument. One of the neck and the implant have a male taper and the other of the neck and the implant have a corresponding female taper, wherein when the male and female tapers are engaged, there is a taper axis. The instrument includes a frame having a distal portion and a proximal portion. The distal portion of the frame includes a retaining member adapted to engage a portion of the neck. The instrument further includes a force applier retained in the proximal portion of the frame, the force applier having an axis that is coaxial with the taper axis. As the force applier is activated, the force applier applies a force on the implant while the neck is held stationary by the frame, thereby causing the male and female tapers to engage.

According to yet another embodiment, a method for assembling a taper between a neck and an implant is provided. The taper has a taper axis. The method includes using an assembly instrument. The assembly instrument includes a frame having a distal portion and a proximal portion. The distal portion of the frame includes a retaining member and a force applier retained in the proximal portion of the frame. The force applier has an axis that is coaxial with the taper axis. The method includes inserting the neck into the retaining member of the frame and inserting the implant into the proximal portion of the frame. The method further includes applying a force to the implant along the force applier axis while the retaining member of the frame holds the neck in place, thereby assembling the tapers.

According to yet another embodiment of the present invention, an instrument for assembling an implant on a neck of a stem is provided. The implant and neck are coupled via a taper having a taper axis. The instrument includes a frame having a distal portion and a proximal portion. The distal portion of the frame includes a retaining member adapted to engage a portion of the neck. The retaining member includes a bracket extending from the distal portion of the frame, and the bracket adapted to engage opposing sides of the neck. A force applier is also included and is retained in the proximal portion of the frame. The force applier has an axis that is coaxial with the taper axis. The force applier is adapted to engage the implant. As the force applier is activated, the force applier applies a force on the implant while the neck is held in place by the frame, thereby causing the tapers of the implant and neck to engage.

According to another embodiment of the present invention, a system for hip orthopaedic surgery is provided. The system includes a stem having a neck, a head, and an instrument. One of the neck and the head have a male taper and the other of the neck and the head have a corresponding female taper, wherein when the male and female tapers are engaged, there is a taper axis. The instrument is adapted to assemble the male and female tapers. The instrument includes a frame having a distal portion and a proximal portion. The distal portion of the frame includes a retaining member adapted to engage a portion of the neck, wherein the retaining member includes a bracket extending from the distal portion of the frame. The bracket is adapted to engage opposing sides of the neck. The instrument further including a force applier retained in the proximal portion of the frame, having an axis that is coaxial with the taper axis. The force applier is adapted to engage the implant. As the force applier is activated, the force applier applies a force on the implant while the neck is held in place by the frame, thereby causing the tapers of the implant and neck to engage.

According to another embodiment of the present invention a method for assembling a taper between a neck and an implant is provided. The taper has a taper axis. The method includes using an assembly instrument, which has a frame having a distal portion and a proximal portion. The distal portion of the frame includes a retaining member. The retaining member includes a bracket extending from the distal portion of the frame. The bracket is adapted to engage opposing sides of the neck. The instrument further includes a force applier retained in the proximal portion of the frame, which has an axis that is coaxial with the taper axis. The method includes inserting the neck into the retaining member of the frame and inserting the implant into the proximal portion of the frame. The method also includes applying a force to the implant along the force applier axis while the frame holds the neck in place, thereby assembling the tapers.

An instrument for assembling a head on a neck of a stem, the implant and neck being coupled via a taper having a taper axis. The instrument includes a frame having a distal portion and a proximal portion. The distal portion of the frame includes a retaining member adapted to engage a portion of the neck. The retaining member includes a pair of moveable arms extending from the distal portion of the frame and the pair of moveable arms adapted to engage a pair of recesses on opposing sides of the neck. The instrument also includes a force applier retained in the proximal portion of the frame, which has an axis that is coaxial with the taper axis. The force applier is adapted to engage the implant. As the force applier is activated, the force applier applies a force on the implant while the neck is held in place by the frame, thereby causing the tapers of the implant and neck to engage.

According to another embodiment, a system for hip orthopaedic surgery is provided. The system includes a stem having a neck, a head, and an instrument. The neck has a pair of tool engagement features. One of the neck and the head have a male taper and the other of the neck and the head have a corresponding female taper, wherein when the male and female tapers are engaged, there is a taper axis. The instrument is for assembling the male and female tapers, and includes a frame having a distal portion and a proximal portion. The distal portion of the frame includes a retaining member adapted to engage the tool engagement features of the neck. The retaining member includes a pair of moveable arms, which are adapted to engage the pair of tool engagement features. The instrument further includes a force applier retained in the proximal portion of the frame, and has an axis that is coaxial with the taper axis. The force applier is adapted to engage the implant, wherein as the force applier is activated, the force applier applies a force on the implant while the neck is held in place by the frame, thereby causing the tapers of the implant and neck to engage.

According to yet another embodiment of the present invention, a method for assembling a taper between a neck and an implant is provided. The taper has a taper axis. The method includes using an assembly instrument, which has a frame having a distal portion and a proximal portion. The distal portion of the frame includes a retaining member. The retaining member includes a pair of moveable arms extending from the distal portion of the frame. The pair of moveable arms are adapted to engage a pair of recesses on opposing sides of the neck. The instrument further includes a force applier retained in the proximal portion of the frame, which has an axis that is coaxial with the taper axis. The method also includes inserting the neck into the retaining member of the frame and inserting the implant into the proximal portion of the frame. A force is applied to the implant along the force applier axis while the retaining member of the frame holds the neck in place, thereby assembling the tapers.

According to anther embodiment of the present invention, an instrument for assembling an implant on a neck of a stem is provided. The stem has a stem axis and the implant and neck being coupled via a taper having a taper axis. The instrument includes a frame having a distal portion, a middle portion having a body axis that is coaxial with the stem axis, and a proximal portion. The distal portion of the frame includes a retaining member adapted to engage a portion of the neck and a connector adapted to engage a corresponding feature of the stem. The instrument also includes a force applier retained in the proximal portion of the frame and having an axis that is coaxial with the taper axis. The force applier is adapted to engage the implant. The force applier axis is not coaxial or parallel with the stem access. As the force applier is activated, the force applier applies a force on the implant while the neck is held in place by the frame, thereby causing the tapers of the implant and neck to engage.

According to yet another embodiment of the invention, a system for hip orthopaedic surgery is provided. They system includes a stem having a neck, a head, and an instrument. One of the neck and the head have a male taper and the other of the neck and the head have a corresponding female taper. When the male and female tapers are engaged, there is a taper axis. The instrument is for assembling the tapers and includes a frame having a distal portion and a proximal portion and a body axis. The distal portion of the frame includes a retaining member adapted to engage a portion of the neck. The instrument further includes a force applier retained in the proximal portion of the frame and has an axis that is coaxial with the taper axis but that is not coaxial or parallel with the stem axis. The force applier is adapted to engage the implant, and as the force applier is activated, the force applier applies a force on the implant while the neck is held in place by the frame, thereby causing the tapers of the implant and neck to engage.

According to yet another embodiment of the present invention, a method for assembling a taper between a neck of a stem and an implant is provided. The taper has a taper axis and the stem having a stem axis. The method includes using an assembly instrument, which has a frame having a distal portion, proximal portion, and a middle portion having a body axis. The distal portion of the frame includes a retaining member. The instrument having a force applier, which has an axis that is coaxial with the taper axis, wherein the force applier axis is not coaxial or parallel with the stem axis. The neck is inserted into the retaining member of the frame and the implant is inserted into the proximal portion of the frame. A force is applied to the implant along the force applier axis while the retaining member of the frame holds the neck in place, thereby assembling the tapers.

DETAILED DESCRIPTION

Any one of the assembly tool embodiments next described may be used during a surgical, hip replacement procedure to assemble a head component to a stem component of a hip replacement prosthesis that is implanted in the proximal femur of a surgical patient. Each of the figures show at least partial views of a hip replacement prosthesis 30, which has a head 2 and a stem 6 that defines a stem axis 18. During a hip replacement surgical procedure, the surgeon implants the distal portion of stem 6 into the intramedullary canal of the proximal femur of the surgical patient. The proximal part of stem 6 includes a neck 8 having a taper 10 that defines a taper axis 20, which is normally oriented relative to stem axis 18 at an angle of about 135 degrees, although this angle may vary. Head 2 includes a taper recess 4 for assembly to taper 10, and the taper design may be a Morse taper or another taper design variation. Head 2 may be spherical or nearly spherical and may be formed from a metal such as, for example, a cobalt chromium alloy, or from a ceramic such as, for example, an aluminum oxide. The size, material, configuration, and surface treatment of each of head 2 and stem 6 depend on the patient anatomy and condition, type of hip replacement prosthesis used (primary or revision), surgical preferences, and other factors. Stem 6 may be formed from a metal such as, for example, a stainless steel or a titanium alloy. Stem 6 may also include a threaded bore 16 (FIG. 2) located in the proximal portion of stem 6 and coaxial with stem axis 18. Threaded bore 16 may be provided for use with conventional, insertion and/or extraction instruments, but may also be used for attachment of the assembly tool, as will be described.

Figure 8:
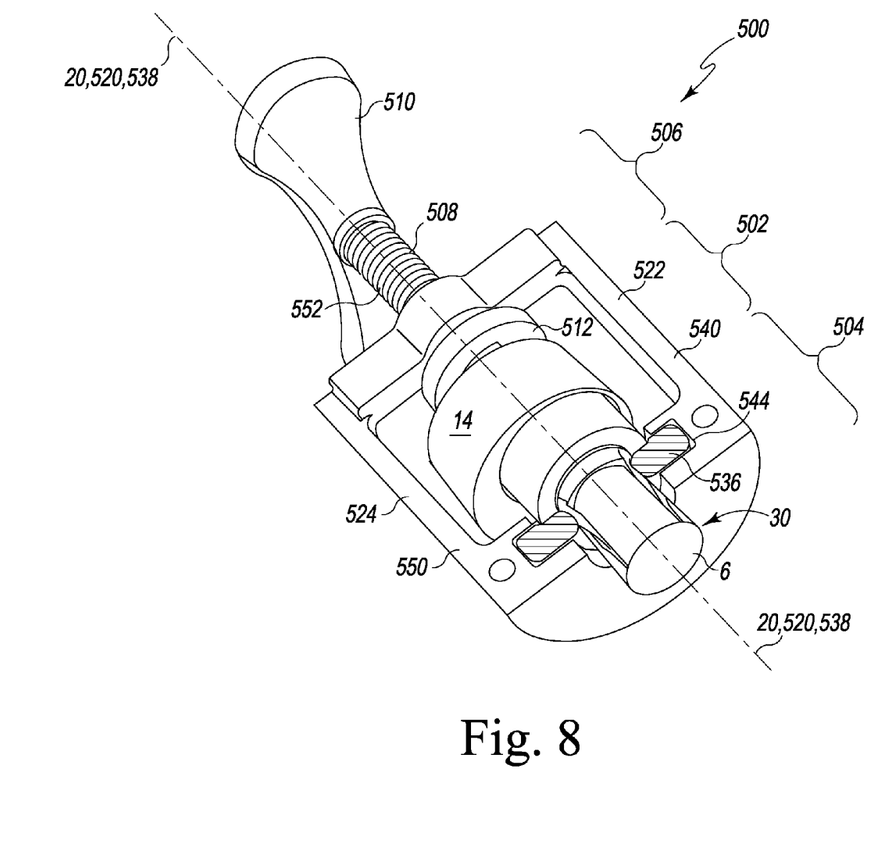
FIG. 8 is a perspective view of a fifth embodiment of the assembly tool, shown as it may be used for assembling an intermediate component and a stem component of a hip replacement prosthesis, showing only the proximal portion of the stem component.

For some types of hip replacement prostheses, an intermediate component may be assembled between the head and the stem, for example, to provide a desired offset from the taper axis. Hip replacement prosthesis 30 of FIG. 8 shows an example of such an intermediate component, an offset component 14 that has both a taper 24 for assembly to head 2 and a taper recess 34 for assembly to stem 6. Each of the assembly tool embodiments herein may easily be adapted for assembling either one of the intermediate component or the head component to the stem component. Another type of intermediate component is a sleeve without an offset feature. A sleeve would also have both a taper for assembly to the head 2 and a tapered recess for assembly to the neck 8 of the stem 6. These types of sleeves are well known in the art.

A user, such as a surgeon or a surgical assistant, may use any one of the assembly tool embodiments next described to apply controllably a sufficient, quasistatic axial force to join the head component to the stem component. A quasistatic axial force shall be understood to be an axial force that is applied gradually, increasing from a low to a high, peak magnitude. Conversely, a quasidynamic axial force shall be understood to be a high axial force that is applied, more or less, instantaneously, such as like a hammer strike.

For each of the following embodiments, the assembly tool generally includes a frame and a force applier. The frame has a proximal portion that supports the force applier for controllably applying a quasistatic force of a desired magnitude to the proximal side of the head, in a direction that is coaxial with taper axis 20. The frame also has a distal portion that removably engages or connects to a proximal part of the stem, thereby providing an opposing, retention force distal to the taper connection, such that substantially no axial force is transmitted to the femur during actuation of the force applier. The assembly tool may be hand operable and can provide at least a peak axial force of about 4 kN. Briefly, the user first hand assembles the head and stem components, then positions and engages the assembly tool onto the head and stem components, and then actuates the assembly tool to complete the assembly of the head and stem components. Once the user has assembled the head and stem components, the user may reversely actuate the force applier and remove the assembly tool from the surgical site.

Figure 1:
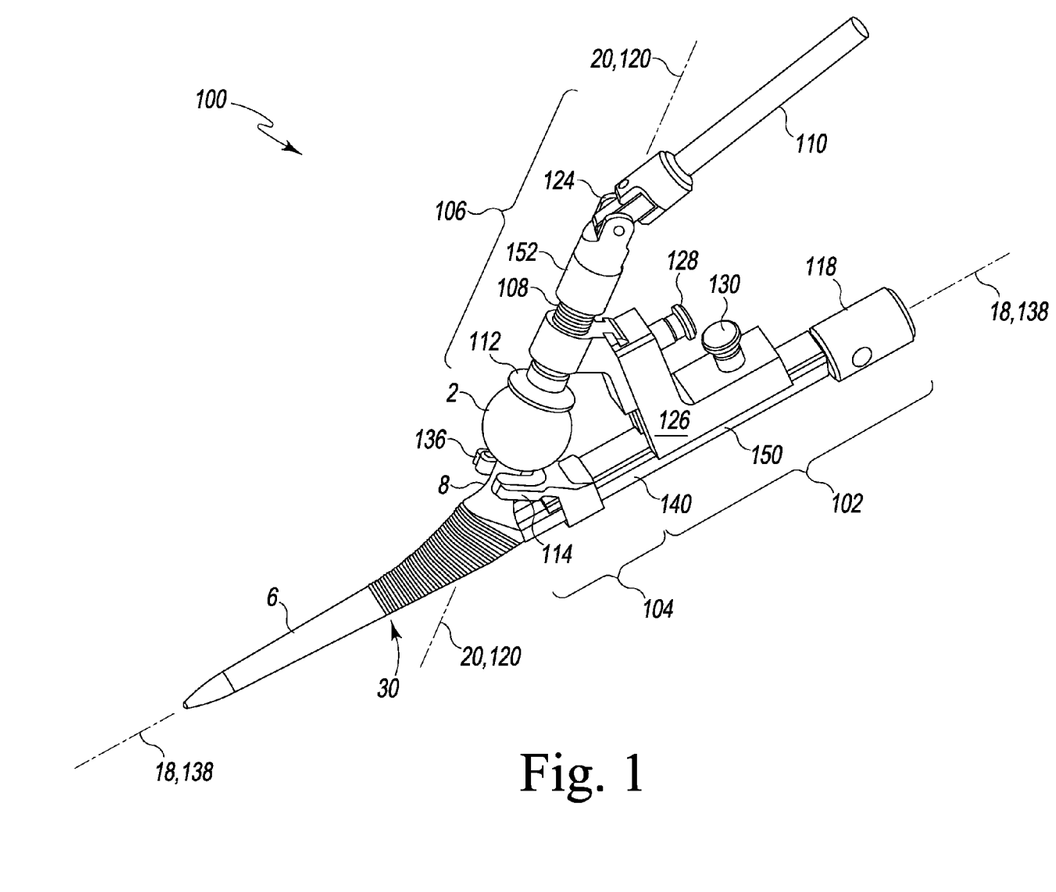
FIG. 1 is a perspective view of a first embodiment of an assembly tool, shown as it may be used for assembling a head component and a stem component of a hip replacement prosthesis.
Figure 2:
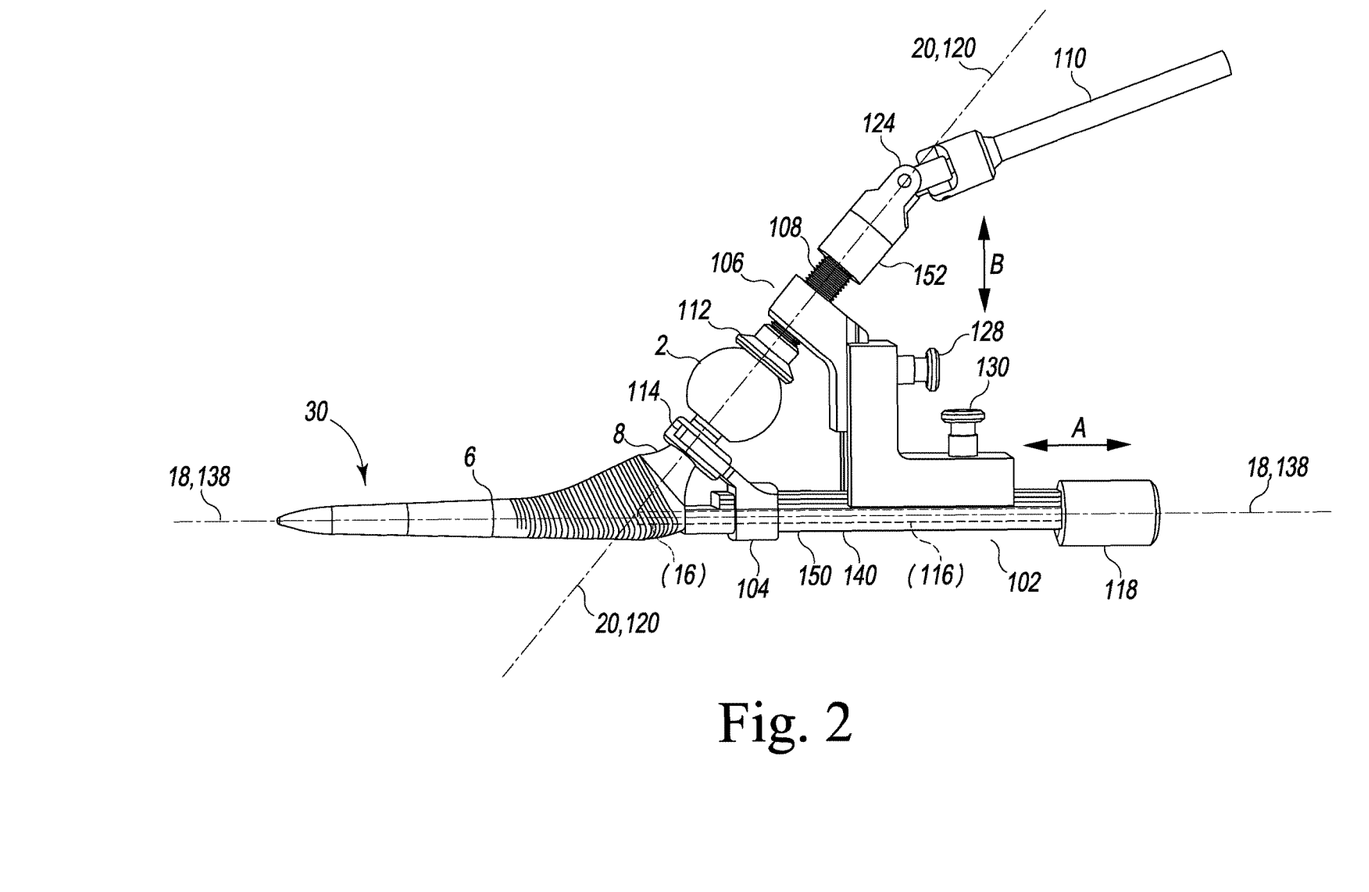
FIG. 2 is a front view of the assembly tool of FIG. 1, shown as it may be used for assembling the head and stem components.

FIG. 1 is a perspective view and FIG. 2 is a front view of a first embodiment of an assembly tool 100, shown as it may be used for assembling together head 2 and a stem 6 of hip replacement prosthesis 30. Assembly tool 100 has a frame 150 with a proximal portion 106 supporting a force applier 152, and a distal portion 104 that is removably attachable to the proximal part of stem 6. Frame 150 is configured such that actuation of force applier 152 provides a quasistatic, axial force along taper axis 20 to the proximal side of head 2, and distal portion 104 provides an opposing, retaining force distal to taper 10 of stem 6, such that substantially no axial force generated by force applier 152 is transmitted to the femur.

A retaining member having a bracket 114 extends from body element 140 in the distal portion 106 of frame 150. Bracket 114 is U-shaped and retains a protective insert 136 that wraps around the opposing sides of neck 8 of stem 6 to stabilize and maintain alignment of frame 150 on stem 6 during actuation of force applier 152.

Force applier 152 has an adjustable screw 108 that defines a screw axis 120 (also referred to as a force applier axis), an actuator 110 for turning screw 108 about force applier axis 120, which is coaxial with taper axis 20, and a foot 112 attached to the distal end of screw 108 for engaging head component 2 of hip replacement prosthesis 30. Proximal portion 104 of frame 150 has an internally threaded throughbore that threadably retains screw 108, such that rotation of screw 108 about screw axis 120 in a first direction advances screw 108 towards head 2 along taper axis 20, and rotation of screw 108 about screw axis 120 in a second direction moves screw 108 away from head 2. Frame 150 also has a middle portion 102 between proximal and distal portions 104, 106. Middle portion 102 has an elongate body 140 defining a body axis 138, which is coaxial with stem axis 18 when frame 150 is attached to stem 6. Body element 140 is hollow and retains a connector, such as a threaded bolt 116 (hidden) that may be threadably inserted into threaded bore 16 of stem 6. The user may rotate, about body axis 138, a bolt knob 118 connected to the proximal end of threaded bolt 116 for threadable and removable attachment of frame 150 to stem 6.

Middle portion 102 also has a carriage 126 that is retained on and adjustably positionable on body 140 in a first direction, as indicated by arrow A. Carriage 126 slidably retains proximal portion 106, which is adjustably positionable on carriage 126 in a second direction that is perpendicular to the first direction, as indicated by arrow B. Carriage 126 has a first screw clamp 128 and a second screw clamp 130 that may be loosened by the user to allow adjustment of proximal portion 106 in the first and second directions, respectively, to align foot 112 and screw axis 120 of force applier 152 with taper axis 20. Once aligned, the user may tighten first and second screw clamps 128, 130 to fix the position of proximal portion 106.

A universal swivel joint 124 bipivotably attaches actuator 110 to screw 108. Actuator 110 is sized and shaped for gripping by the user for applying sufficient torque to screw 108 to achieve the desired, peak axial force.

Foot 112 may be formed from a non-metallic material such as a polymer or an elastomer to prevent damage to head 2. Foot 112 may be rotatably attached to the end of screw 108 such that upon reaching a certain applied axial force, screw 108 turns about screw axis 120 in foot 112. Alternately, foot 112 may be fixedly attached to the end of screw 108, such that foot 112 and screw 108 always rotate together about screw axis 108 during actuation of force applier 152.

Figures 3, 4:
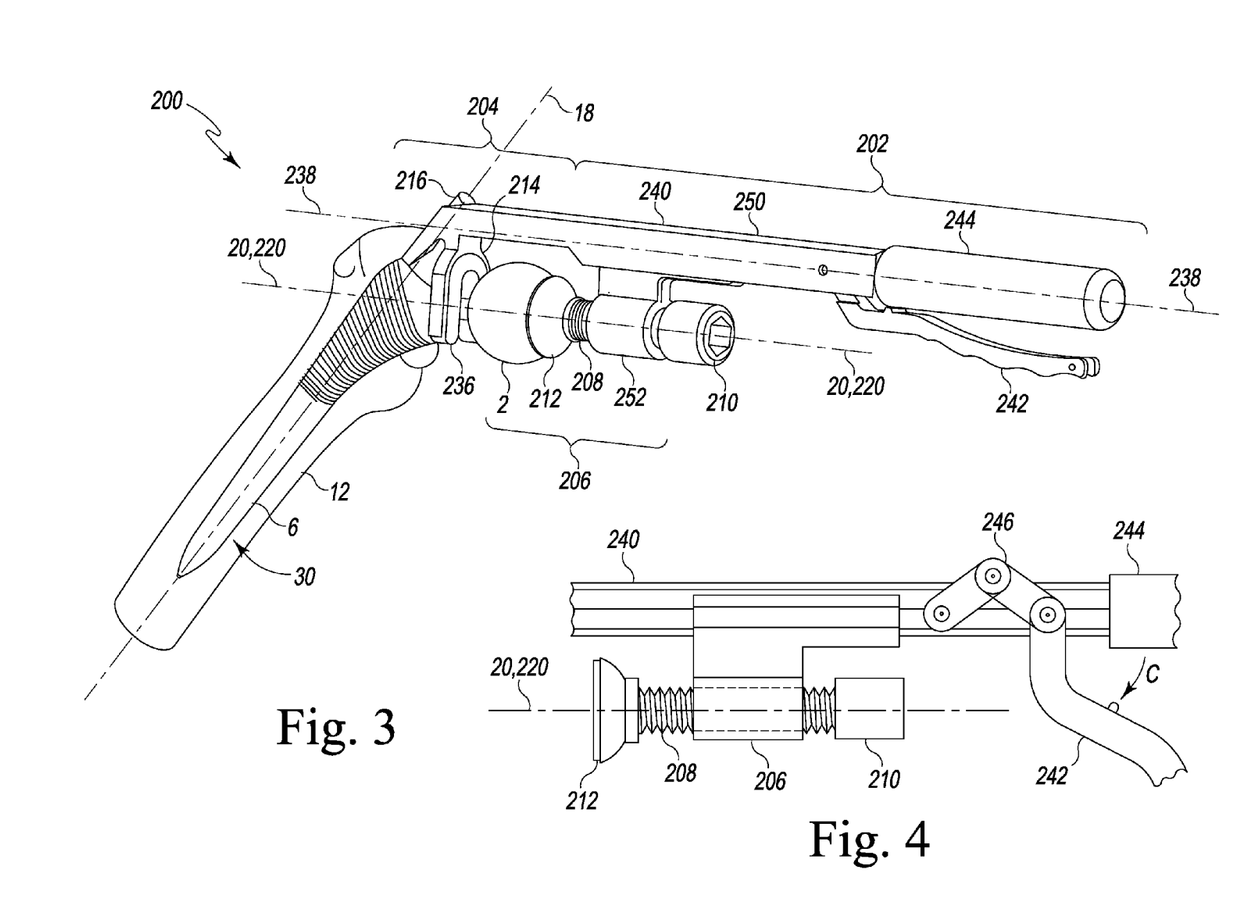
FIG. 3 is a perspective view of a second embodiment of the assembly tool, shown as it may be used for assembling the head and stem components, while the stem is positioned in the femur of a surgical patient.
FIG. 4 is a detailed, internal view of a portion of the assembly tool shown in FIG. 3, showing a quick release mechanism.

FIG. 3 is a perspective view of a second embodiment, assembly tool 200, shown as it may be used for assembling head 2 onto stem 6 while stem 6 is positioned in the femur. Assembly tool 200 has a frame 250 with a proximal portion 206 supporting a force applier 252, and a distal portion 204 that is removably attachable to threaded bore 16 (see FIG. 2) of stem 6 using a bolt 216. The force applier 252 may be adjustable to implant various head sizes and offsets. Frame 250 is configured such that actuation of force applier 252 provides a quasistatic, axial force along taper axis 20 to the proximal side of head 2, and distal portion 204 provides an opposing, retaining force distal to taper 10 of stem 6, such that substantially no axial force generated by force applier 252 is transmitted to the femur.

Frame 250 also has a middle portion 202 between proximal portion 206 and distal portion 204. Middle portion 202 has a body 240 defining a body axis 238. Body 240 slidably retains proximal portion 206 for movement between a first position (shown in FIG. 4) and a second position (shown in FIG. 3). A hand grip 244 extends from the proximal end of body element 240 along body axis 238. A quick-release actuator 242 pivotably attaches to the proximal end of body element 240, such that the user may operate it using the same hand that is holding hand grip 244. A linkage 246, shown in FIG. 4, operationally connects quick-release actuator 242 to proximal portion 206. In the second position, linkage 246 is in a locked orientation so that actuation of force applier 252 does not move proximal portion 206 away from head 2.

Proximal portion 206 has a threaded throughbore (hidden) and threadably retains a screw 208 that defines a screw axis 220. A foot 212 is attached to the distal end of screw 208 and is similar to foot 112 of assembly tool 100. An actuator 210 is a hex-drive screw head and may be driven by a conventional, surgical, hex-drive tool (not shown) to rotate screw 208 about screw axis 220 in a first direction to move foot 212 along screw axis 220 and towards head 2, and in a second direction to move foot 212 along screw axis 220 and away from head 2. The hex-drive tool may be a torque-limiting tool so that the desired, peak axial force may not be exceeded.

A retaining member includes a bracket 214 with a protective insert 236 extends from distal portion 204 and is U-shaped to wrap around the sides of neck 8 of stem 6 to help stabilize and maintain alignment of frame 250 during actuation of force applier 252.

Figures 5, 6:
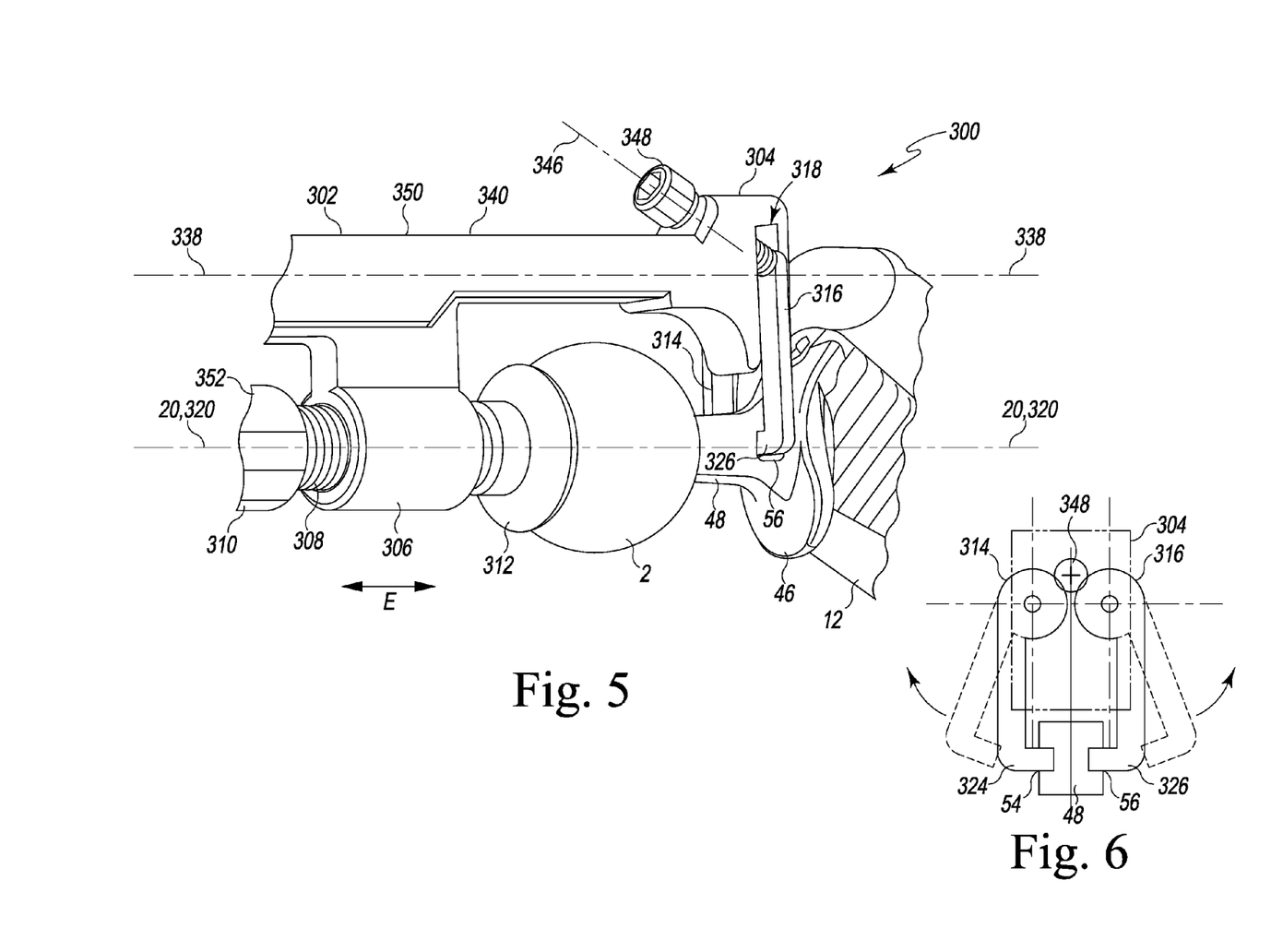
FIG. 5 is a perspective view of a third embodiment of the assembly tool, shown as it may be used for assembling the head and stem components, while the stem is positioned in the femur of a surgical patient.
FIG. 6 is a detailed, partial, sectional view of the assembly tool shown in FIG. 5, showing how a pair of opposing arms may be drawn together about the stem component.

FIG. 5 is a perspective, partial view of a third embodiment, assembly tool 300, shown as it may be used for assembling head 2 and stem 6 after stem 6 has been inserted into the proximal femur. Assembly tool 300 is similar to assembly tool 200 of FIG. 3, differing only by the attachment means to stem 6.

Assembly tool 300 has a frame 350 with a proximal portion 306, a distal portion 304, and a middle portion 302. Proximal portion 306 threadably retains a force applier 352, which has a screw 308 that defines a screw axis 320, a foot 312, and an actuator 310 (partially shown). Screw axis 320 is coaxial with taper axis 20. Middle portion 302 has a body 340 that defines a body axis 338, which is spaced apart from and parallel to screw axis 320. Body 340 slideably retains proximal portion 306, which is adjustably positionable on body element 340 between a first and a second position, as indicated by arrow E.

Distal portion 304 has a retaining member having a slot 318 that retains a first arm 314 and an opposing, second arm 316, each of which extend perpendicularly from body axis 338. Each of arms 314, 316 is pivotably attached to distal portion 304, such that arms 314, 316 can swing independently of each other within the same plane as shown in FIG. 6. Distal portion 304 threadably retains a locking screw 348, which defines a lock screw axis 346 and which is oriented with respect to arms 314, 316, such that when screw 348 is advanced along screw axis 346, the tip (which may be conically shaped) of screw 348 drives between arms 314, 316 to draw arms 314, 316 together. Conversely, loosening screw 348 in the opposite direction allows arms 314, 316 to open.

Assembly tool 300 may only be used with a stem component having compatible, tool engagement features. A first engagement recess 54 and a second engagement recess 56 are located on opposing sides of a neck 48 of a modified, stem 46, such that taper axis 20 extends approximately between them. First and second engagement recesses, 54, 56, may be formed into stem 46 to a relatively shallow depth, for example 1-3 mm, and have any one of a number of possible profiles, such as, for example, rectangular, circular, or D-shape. Each of a first tip 324 of arm 314 and a second tip 326 of second arm 316 may be configured to fit snuggly within either of recesses 54, 56 of stem 6. To attach frame 350 to stem 46, the user positions tips 324, 326 of arms 314, 316 over recesses 54, 56, of neck 48, respectively, when arms 314, 316 are open, while centering foot 312 over head 2. The user then tightens arms 314, 316 using a conventional drive tool to advance screw 348 along screw axis 346, so that tips 324, 326 tightly clamp into recesses 54, 56, thereby forming a rigid connection between frame 350 and stem 46. The user may then position foot 312 onto head 2 and actuate force applier 352 to complete the assembly of head 2 to stem 46. The user may grip frame 350 with one hand to stabilize it while using the other hand to actuate force applier 352.

Figure 7:
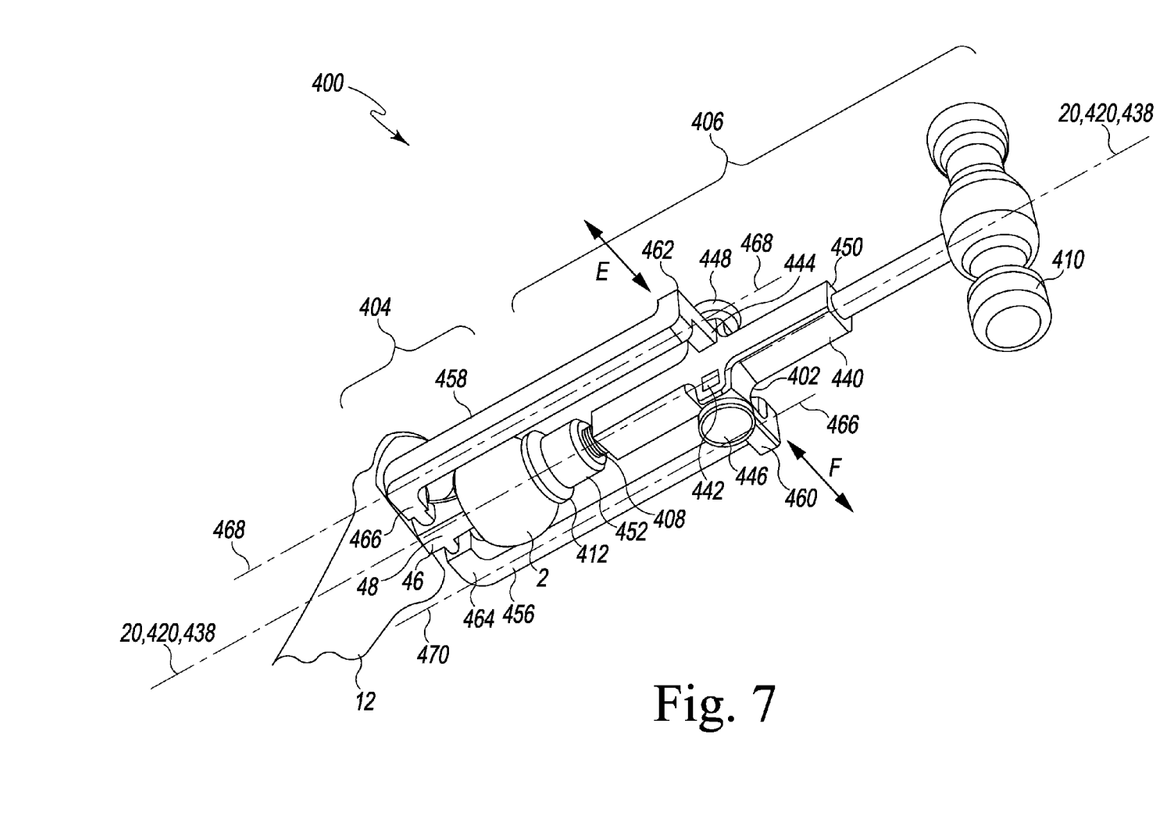
FIG. 7 is a perspective view of a fourth embodiment of the assembly tool, shown as it may be used for assembling the head and stem components, while the stem is positioned in the proximal femur of a surgical patient.

FIG. 7 is a perspective view of a fourth embodiment, assembly tool 400, shown as it may be used for assembling head 2 onto stem 46 while stem 46 is positioned in the proximal femur. Assembly tool 400 has a frame 450 with a proximal portion 406, a middle portion 402, and a distal portion 404. Proximal portion 406 retains a force applier 452, which has a screw 408 defining a screw axis 420, a foot 412, and an actuator 410. Proximal portion 406 has a body 440 with an internally threaded bore that threadably retains screw 408. Body 440 defines a body axis 438. Both body axis 438 and screw axis 420 are coaxial with taper axis 20. The user may grip and turn actuator 410 in a first rotational direction about screw axis 420 to advance screw 408 towards head 2, and in the opposite, second rotational direction to move screw 408 away from head 2.

Body 440 has a first channel 442 that slidably retains a first elongate arm 456 defining a first arm axis 468. Body 440 also has a second channel 444 that slidably retains a second elongate arm 458 defining a second arm axis 470. First and second arm axis 468, 470 are parallel to body axis 420. The proximal ends (analagous to a person's "shoulders") of first and second elongate arms 456, 458 are mounted on opposing sides of body 440. First elongate arm 456 is positionable in a direction perpendicular to body axis 438, as indicated by arrow F. Second elongate arm 458 is positionable in a direction perpendicular to body axis 438, as indicated by arrow E. A first screw clamp 448 and a second screw clamp 446 allow the user to independently position and fix each of first and second elongate arms, 456, 458, respectively, at a desired, spaced apart position, relative to body axis 438.

Assembly tool 400 may only be used with a stem component having compatible, tool engagement features, such as described for assembly tool 300. First and second recesses, 54, 56 of stem 46 may be employed as anchoring locations for the distal ends (analagous to "hands"), of first and second elongate arms 456, 458. The user may assemble head 2 onto stem 46 in a manner similar to that described for assembly tool 300.

Figure 9:
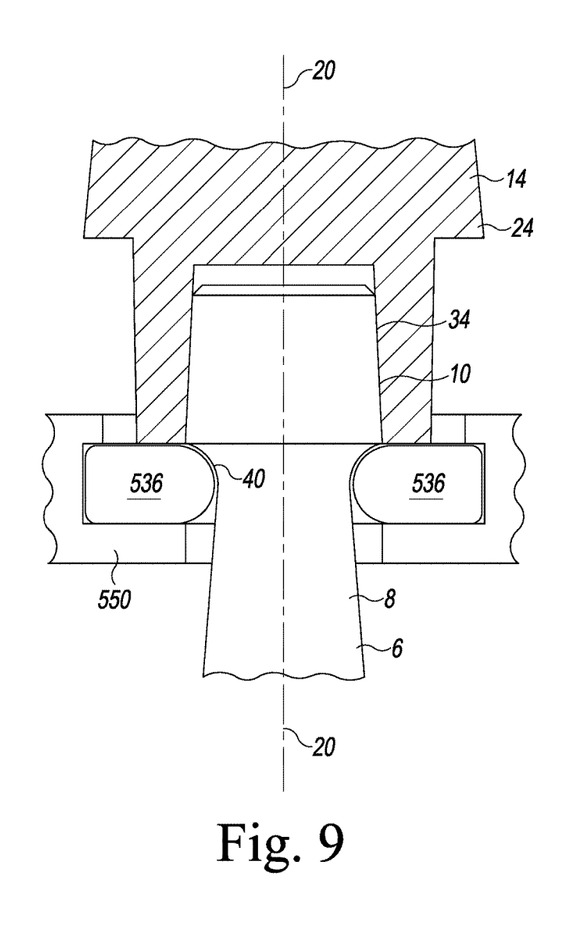
FIG. 9 is a sectional view of a portion of the assembly tool shown in FIG. 8, showing the intermediate component assembled onto a taper of the stem component, and a first embodiment of a protective insert.

FIG. 8 is a perspective view and FIG. 9 is a partial view of a fifth embodiment, assembly tool 500, shown as it may be used for assembling intermediate component 14 (shown in a sectional view) onto stem 6 of hip replacement prosthesis 30 (showing only the proximal portion). Assembly tool 500 has a frame 550 with a proximal portion 506, a middle portion 502, and a distal portion 504. Proximal portion 506 retains a force applier 552 having a screw 508 defining a screw axis 520, an actuator 510, and a foot 512. Middle portion has a body 540 that has a first arm 522 and a second arm 524, each of which is fixed and equally spaced apart from a body axis 538. Screw axis 520 and body axis 538 are coaxial with taper axis 20. Distal portion 504 has a retaining member, which in this embodiment is a semicircular, annular groove 544 that retains a first embodiment, protective insert 536. Frame 550 is rigid and configured (like half of an "open clamshell") to allow positioning of assembly tool 500 onto hand-assembled, offset component 14 and neck 8 of stem 6, even if stem 6 has already been fully inserted into the proximal femur. Protective insert 536 is sized and shaped to conform to a neck contour 40 that is immediately distal to taper 10 of neck 8. Protective insert 536 may be formed from a non-metallic, biocompatible, sterilizable material, such as PEEK, UHMWPE, polycarbonate, or any of a number of available, engineering plastics. The user may use assembly tool 500 in a very similar manner as previously described for the other embodiments.

Figure 10:
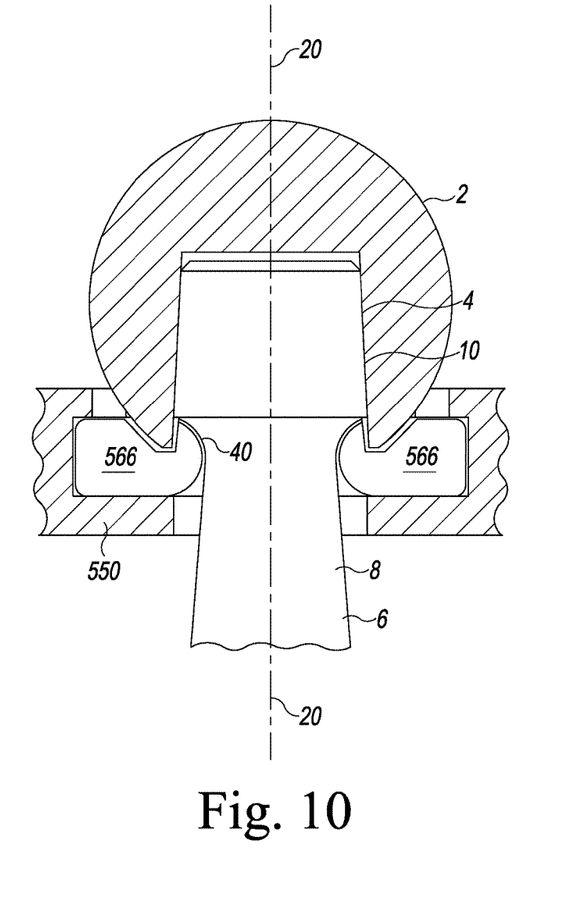
FIG. 10 is a sectional view of a portion of the assembly tool shown in FIG. 8, showing the head component assembled onto the taper of the stem component, and a second embodiment of the protective insert.

FIG. 10 is a partial view of assembly tool 500, shown as it may be used for assembling head 2 (shown in a sectional view) onto stem 6 (showing only the proximal portion). Assembly tool 500 is shown with a second embodiment, protective insert 566, which is configured to extend partially into taper recess 4 of head 2. Protective insert 566 provides for situations in which taper 10 is shorter than taper recess 4, and upon assembly, head 2 "hangs" over neck 8 a small distance.

Figure 11:
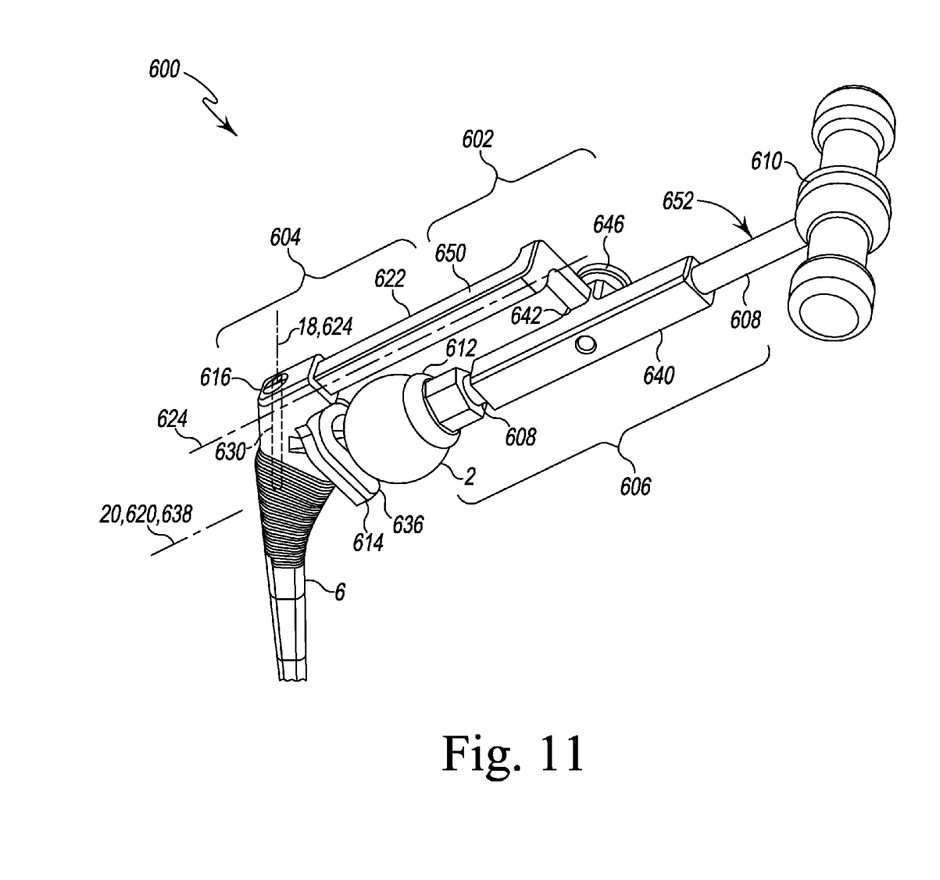
FIG. 11 is a perspective view of a sixth embodiment of the assembly tool.

FIG. 11 is a perspective view of a sixth embodiment, an assembly tool 600, as a surgeon may position it to assemble head 2 onto stem 6. Similar to the previous embodiments, assembly tool 600 has a frame 650 that is removably attachable to stem 6, and a force applier 652 for the controllable application of a clamping force to head 2 along taper axis 20. Force applier 652 has an elongate screw 608 defining a screw axis 620, an actuator 610 attached to the proximal end of screw 608, and a foot 612 attached to the distal end of screw 608.

Frame 650 has a distal portion 604, a middle portion 602, and a proximal portion 606. Distal portion 604 has a connector 616 for the removable attachment of frame 650 to stem 6. As previously described for assembly tool 100 (FIG. 1), the proximal body of stem 6 may be provided with a threaded bore, coaxial with stem axis 16, for the attachment of an insertion and/or extraction instrument. If stem 6 is provided with such a threaded bore, connector 616 may be a threaded bolt inserted through a counterbored through-hole 630 in distal portion 604. Counterbored through-hole 630 defines a hole axis 624. During the surgical procedure, the surgeon may use a conventional driver to tighten connector 616 when attaching frame 650 to stem 6, and to loosen connector 616 when removing frame 650 from stem 6. However, those skilled in the art will appreciate that connector 616 may be any one of numerous types of mechanical elements/mechanisms adapted to removably attach to any one of numerous types of slots, recesses, undercut holes, and the like, that may be provided in the proximal stem body, either specifically for use with assembly tool 600 or for alternate purposes, such as for the insertion and/or an extraction of the stem. For each of these arrangements, the surgeon may use connector 616 to achieve a secure, removable attachment of frame 650 to stem 6, in order to provide a retention force that opposes the applied clamping force, thereby minimizing the transfer of force to the femur during actuation of force applier 652.

Distal portion 604 of frame 650 also includes a bracket 614 that helps to maintain the correct alignment of frame 650 with respect to taper axis 20 during the application of the clamping force using force applier 652. As described for assembly tool 100 (FIG. 1), bracket 614 may be provided with a protective insert 636 that helps prevent damage to the surface of the neck of stem 6. Bracket 614 is U-shaped for easy positioning around the neck of stem 6 prior to attaching connector 616 to stem 6, and for removal of assembly tool 600 from stem 6 after assembly of head 2 onto stem 6.

Proximal portion 606 of frame 650 has a body 640 defining a body axis 638. Body 640 is generally tubular and has an internal screw thread (hidden in FIG. 12) extending at least along a portion of the length of body 640. Body 640 threadably retains screw 608 of force applier 652, such that screw axis 620 is coaxial with taper axis 20 when assembly tool 600 is properly positioned for actuation of force applier 652.

To actuate force applier 652, the surgeon rotates actuator 610 in a first direction (i.e., clockwise) to move foot 612 along taper axis 20 and towards head 2. Conversely, to deactuate force applier 652, the surgeon rotates actuator 610 in a second direction (i.e., counterclockwise) to loosen and remove force applier 652 from head 2. Actuator 610 may have a T-bar configuration as shown in FIG. 12. The size and shape of actuator 610 may be based on ergonometric data known in the art, so that a person with average hand/arm strength could easily apply the necessary torque to achieve at least a predetermined, desired clamping force. Alternatively, actuator 610 may be provided with a torque-limiting mechanism, of which numerous types are well-known in the mechanical, hand tool industry, such that it would be impossible for the surgeon to apply a clamping force that exceeds the predetermined, desired force. The actual magnitude of the predetermined, desired force may be recommended by the implant manufacturer, and be based on the appropriate testing and analysis of the taper connection.

Proximal portion 604 and middle portion 602 of frame 650 define an arm axis 624 that is parallel and offset from screw axis 620. As shown in FIG. 12, middle portion 602 may be configured to be slidably retained in a channel 642 of body 640. The surgeon may loosen a screw clamp 646 to adjust the offset of arm axis 624 relative to screw axis 620, such as may be desirable for different sizes and configurations of stem and head components. The surgeon may then tighten screw clamp 646 to maintain a rigid attachment of middle portion 602 to body 640. This ability to separate proximal portion 606 from middle portion 602 also may be advantageous for cleaning/sterilizing assembly tool 600 or for more efficiently storing assembly tool 600 in a surgical tray. Alternatively, middle portion 602 may be fixedly attached to body 640, in which case foot 612 may be designed to accommodate various stem configurations and head sizes. In the latter arrangement, for example, foot 612 may be rigidly attached to screw 608 and have a flat face for interfacing against head 2, thereby allowing slight misalignment of screw axis 620 and taper axis 20.

Each component of assembly tool 600 may be formed from any one of numerous types of stainless steels or biocompatible polymers commonly used for multiple-use and single-use, surgical instruments. Protective insert 636 and foot 612 may be formed from a biocompatible polymer, for example PEEK, which is softer than the implant materials, in order to prevent damage to the implant surfaces. Protective insert 636 may also be formed from a biocompatible elastomer, such as silicone rubber, that is retained on or bonded to bracket 614.

As those skilled in the art will appreciate, there are many variations of the assembly tool embodiments described herein. For example, any of them may have an actuator that incorporates a force limiting mechanism to prevent applying excessive torque while actuating the force applier. Also, any of them may have one or more additional grips or handles extending from or incorporated into the assembly tool frame to help maintain stability and alignment of the assembly tool while actuating the force applier. Also, each of the assembly tool embodiments may be designed to be either one of a single-use (disposable) or a multiple-use (reusable) device. Also, in addition to mechanical, screw-driven types of force appliers, other types of force appliers may include, for example, the following: mechanical, ratcheting types; hydraulically driven types; pneumatically driven types; expanding gas-driven types (incorporating, for example, a small, disposable cannister of carbon dioxide gas); electrical, motor-driven gear mechanism types; and mechanical, linkage driven types. An assembly tool having any one of these types of force appliers can provide the user with the ability to controllably apply a quasistatic, axial force that has the desired, peak magnitude (such as about 1000 pounds/5000 N) and that is directed along the taper axis of the head and stem components to fully join those components.

What is claimed is:

1. An instrument for assembling an implant on a neck, the implant and neck being coupled via a taper having a taper axis, the instrument comprising:
   a frame having a distal portion and a proximal portion, the distal portion of the frame including a retaining member adapted to engage a portion of the neck; and
   a force applier retained in the proximal portion of the frame, the force applier including a screw having a screw axis that is coaxial with the taper axis, wherein the screw is adapted to engage the implant;
   wherein as the screw is turned, the force applier applies a force on the implant while the neck is held in place by the frame, thereby causing the tapers of the implant and neck to engage and wherein the retaining member of the frame includes an annular groove and a protective insert adapted to protect the neck from being scratched by the frame.

2. The instrument of claim 1, wherein the frame also includes a middle portion, the middle portion having a body with a first arm and a second arm spaced apart from the screw axis.

3. The instrument of claim 1, wherein the proximal portion further includes an actuator coupled to the screw, wherein the actuator is adapted to enable a user to turn the screw.

4. The instrument of claim 3, wherein the actuator is a handle.

5. The instrument of claim 1, wherein the proximal portion further includes a foot adapted to engage the implant.

6. A system for hip orthopaedic surgery comprising:
   a neck;
   an implant, wherein one of the neck and the implant have a male taper and the other of the neck and the implant have a corresponding female taper, wherein when the male and female tapers are engaged, there is a taper axis; and
   an instrument, the instrument including a frame having a distal portion and a proximal portion, the distal portion of the frame including a retaining member adapted to engage a portion of the neck, the instrument further including a force applier retained in the proximal portion of the frame, the force applier having an axis that is coaxial with the taper axis;
   wherein as the force applier is activated, the force applier applies a force on the implant while the neck is held stationary by the frame, thereby causing the male and female tapers to engage and wherein the retaining member of the frame includes an annular groove and a protective insert adapted to protect the neck from being scratched by the frame.

7. The system of claim 6, wherein the force applier is a screw and the proximal portion of the frame further includes an actuator coupled to the screw, wherein the actuator is adapted to enable a user to turn the screw.

8. The system of claim 7, wherein the actuator is a handle.

9. The system of claim 6, wherein the proximal portion further includes a foot adapted to engage the implant.

10. The system of claim 6, wherein the frame also includes a middle portion, the middle portion having a body with a first arm and a second arm spaced apart from the force applier axis.

11. The system of claim 6, wherein the implant is an insert.

12. The system of claim 6, wherein the implant is a femoral head.

* * * * *